United States Patent
Kobayashi et al.

(10) Patent No.: US 9,230,323 B2
(45) Date of Patent: Jan. 5, 2016

(54) X-RAY DIAGNOSTIC APPARATUS AND X-RAY DIAGNOSTIC METHOD

(71) Applicants: KABUSHIKI KAISHA TOSHIBA, Minato-Ku (JP); TOSHIBA MEDICAL SYSTEMS CORPORATION, Otawara (JP)

(72) Inventors: Tadaharu Kobayashi, Otawara (JP); Toshiya Waku, Yaita (JP); Keisuke Nakamura, Utsunomiya (JP); Kenji Mizutani, Nasushiobara (JP)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 14/714,811

(22) Filed: May 18, 2015

(65) Prior Publication Data

US 2015/0332455 A1    Nov. 19, 2015

(30) Foreign Application Priority Data

May 19, 2014    (JP) ................................. 2014-103662

(51) Int. Cl.
   *G06K 9/00*    (2006.01)
   *G06T 7/00*    (2006.01)
   *A61B 6/00*    (2006.01)

(52) U.S. Cl.
   CPC ............... *G06T 7/0012* (2013.01); *A61B 6/481* (2013.01); *A61B 6/486* (2013.01); *A61B 6/504* (2013.01); *A61B 6/5217* (2013.01); *A61B 6/542* (2013.01); *G06T 2207/10016* (2013.01); *G06T 2207/30101* (2013.01)

(58) Field of Classification Search
   CPC ...... A61B 5/055; A61B 5/7285; A61B 6/027; A61B 6/03; A61B 6/481; A61B 6/541; A61B 8/481; A61B 8/543
   See application file for complete search history.

(56) References Cited

U.S. PATENT DOCUMENTS

| | | | | |
|---|---|---|---|---|
| 6,647,283 B2 * | 11/2003 | Klotz | ..................... | A61B 6/481 378/21 |
| 8,755,865 B2 * | 6/2014 | Gonzalez Molezzi | . | A61B 6/481 600/427 |
| 2012/0236995 A1 * | 9/2012 | Eusemann | ............... | A61B 6/03 378/108 |
| 2014/0005538 A1 * | 1/2014 | Florent | .................. | A61B 6/503 600/431 |

FOREIGN PATENT DOCUMENTS

| | | |
|---|---|---|
| JP | 2006-034952 | 2/2006 |
| JP | 2009-207876 | 9/2009 |
| JP | 2014-012133 | 1/2014 |

* cited by examiner

*Primary Examiner* — Tom Y Lu
(74) *Attorney, Agent, or Firm* — Oblon, McClelland, Maier & Neustadt, L.L.P.

(57) ABSTRACT

According to one embodiment, an X-ray diagnostic apparatus includes processing circuitry. The processing circuitry generates a plurality of contrast images sequentially based on X-rays after administration of a contrast medium to the object, determines a monitoring region in the plurality of contrast images, monitors change in signal strength of each of pixels included in the monitoring region, and determines whether or not the signal strength of each of the pixels included in the monitoring region satisfies a specified condition. The processing circuitry controls an X-ray generator based on a result of the determination so as to reduce an X-ray dose or turn off irradiation. The processing circuitry generates a parametric image based on a feature amount determined by change in signal strength of each of pixels of a part of the plurality of contrast images sequentially generated before the X-ray generator is controlled based on the result of the determination.

20 Claims, 9 Drawing Sheets

X-RAY DIAGNOSTIC APPARATUS AND X-RAY DIAGNOSTIC METHOD

CROSS-REFERENCE TO RELATED APPLICATIONS

This application claims the benefit of priority of Japanese Patent Application No. 2014-103662, filed May 19, 2014, the entire contents of which are incorporated herein by reference.

FIELD

Embodiments described herein relate generally to an X-ray diagnostic apparatus and an X-ray diagnostic method.

BACKGROUND

Angiographic images acquired with X-ray diagnostic apparatuses can facilitate observation of blood vessels. With such angiographic images, medical treatment planning and operations can be conducted based on detailed information on blood circulatory systems in a heart and/or a brain. Such angiographic images are used, for example, in operations such as for removal of emboli in blood vessels, removal of aneurysms, and dissolution of stenosis with indwelled stents. In these operations, the angiographic images are used to confirm the form of blood vessels, focuses, postoperative blood flow, and the like. The operations with use of angiographic images are performed by using a catheter inserted from a blood vessel of a region such as a femoral region and a cervical region. As compared with general surgical operations, the operations using angiographic images have little burden on patients and provide high Quality Of Life (QOL). This makes the angiography an indispensable clinical technique.

A digital subtraction angiography (DSA) is known as a technique for acquiring angiographic images by X-ray diagnostic apparatuses. The DSA is to obtain a difference between a pre-contrasting image (hereinafter referred to as a mask image) and an image after introduction of a contrast medium (hereinafter referred to as a contrast image) so that the contrast medium introduced into blood vessels of a patient is highlighted for clear visualization of the blood vessels.

According to the DSA image (hereinafter referred to as an angiographic image) obtained from the difference between the mask image and the contrast image, not only the form of blood vessels can be acquired, but also various information pieces, such as blood flow velocities and blood flow rates, can be acquired based on transmit time of the contrast medium, and the like. For example, dynamics of the injected contrast medium can be captured by creating a Time Density Curve (TDC) based on signal strength of each pixel of angiographic images. Based on the TDC, various information pieces can be acquired, such as Time to Peak (TP) which represents the time when the concentration of the contrast medium in each pixel becomes a maximum, Arrival Time (AT) which represents the time when the contrast medium starts to dye, and Mean Transit Time (MTT) which represents a mean passing time of the contrast medium. For visually displaying these various information pieces, there is a method called parametric imaging (PI) which images various parameters, such as aforementioned TP, AT, and MTT. The PI provides a technique to generate color maps which express various parameter information in the form of change in color and/or brightness.

However, in DSA imaging, X-rays are emitted like a pulse to enable tens of images to be taken in one second. In the DSA imaging, imaging is performed with a relatively high X-ray intensity for the purpose of reducing noise and providing a high contrast resolution. Furthermore, PI images are acquired by successive observation of the dynamics of the contrast medium in blood vessels. Therefore, it takes longer time to perform the DSA imaging, which increases a radiation dose of the patient. In operations relating to blood vessels and/or a circulatory system, DSA imaging needs to be performed at least twice, once before treatment and once after treatment. This also causes undesirable increase in the radiation dose.

Accordingly, an X-ray diagnostic apparatus with a low X-ray radiation dose is demanded.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray diagnostic apparatus and X-ray diagnostic method according to embodiments of the present invention with reference to the drawings.

In general, according to one embodiment, the X-ray diagnostic apparatus includes an X-ray generator and processing circuitry. The X-ray generator generates X-rays for irradiating an object. The processing circuitry generates a plurality of contrast images sequentially based on the X-rays after administration of a contrast medium to the object. The processing circuitry determines a monitoring region in the plurality of contrast images. The processing circuitry monitors change in signal strength of each of pixels included in the monitoring region of the plurality of contrast images sequentially generated. The processing circuitry determines whether or not the signal strength of each of the pixels included in the monitoring region satisfies a specified condition. The processing circuitry controls the X-ray generator based on a result of the determination so as to reduce an X-ray dose or to turn off irradiation of the X-rays. The processing circuitry generates a parametric image based on a feature amount determined by change in signal strength of each of pixels of a part of the plurality of contrast images sequentially generated, the part of the plurality of contrast images sequentially generated being generated before the X-ray generator is controlled based on the result of the determination.

(1) Configuration

Figure 1:
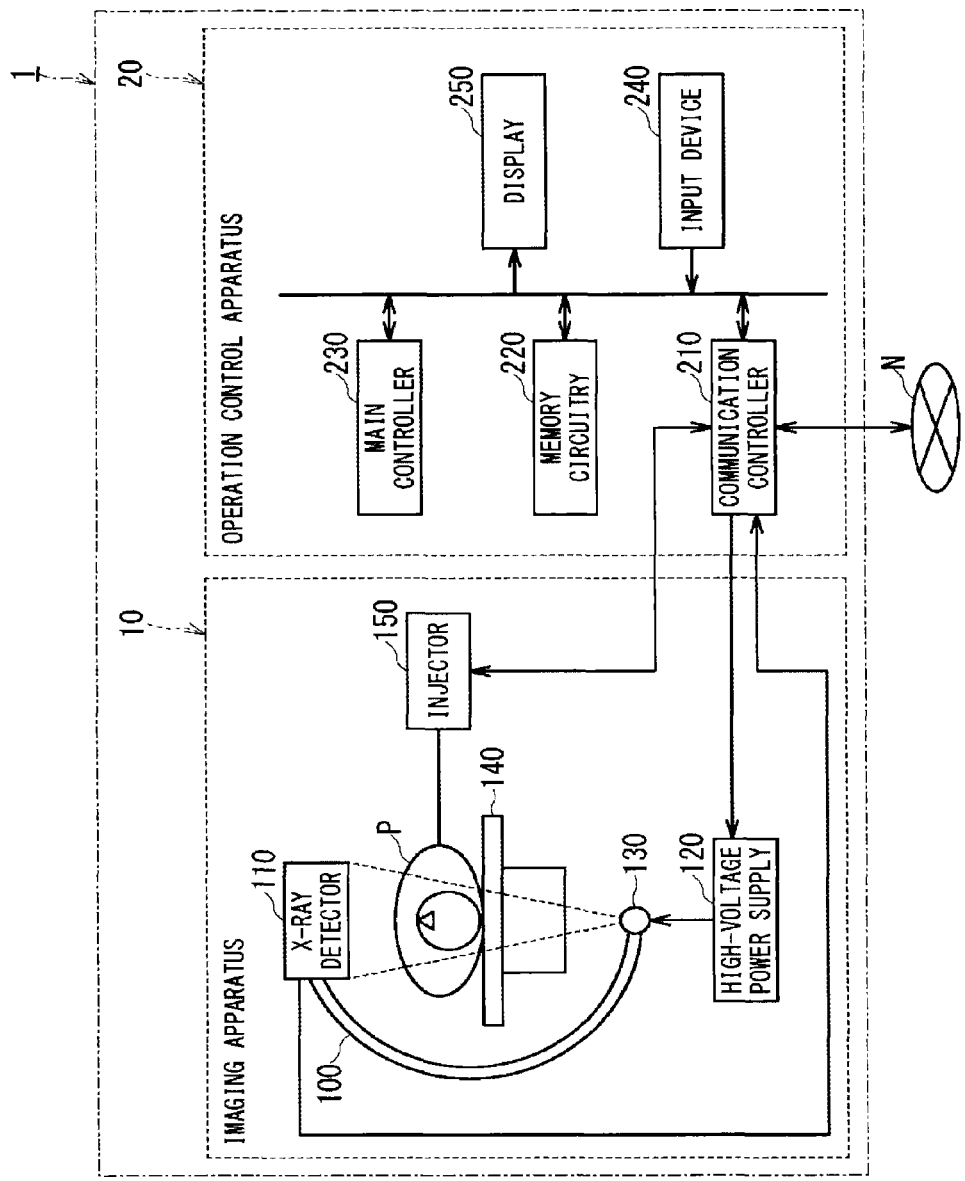
FIG. 1 is a conceptual block diagram illustrating one example of the X-ray diagnostic apparatus according to the embodiment.

FIG. 1 is a conceptual block diagram illustrating one example of the X-ray diagnostic apparatus according to the embodiment. The X-ray diagnostic apparatus 1 illustrated in FIG. 1 includes an imaging apparatus 10 and an operation control apparatus 20. Image data imaged in the imaging apparatus 10 is transmitted to the operation control apparatus 20. The operation control apparatus 20 performs imaging control, and in addition, performs such operation as generation of angiographic images based on the image data imaged in the imaging apparatus 10. The angiographic images are difference images between image data before contrasting (mask images) and image data after contrasting (contrast image).

The imaging apparatus 10 of the X-ray diagnostic apparatus 1 according to the present embodiment may be configured to include a single plain X-ray imaging apparatus as illustrated in FIG. 1, and may be configured to include a biplane X-ray imaging apparatus. The imaging apparatus 10 is not limited to the X-ray imaging apparatus but may be an MRI apparatus and/or an X-ray computed tomography (CT) apparatus capable of providing contrast images of a vascular system.

First, the imaging apparatus 10 will be described. The imaging apparatus 10 as an imaging system is constituted of an X-ray detector 110 and an X-ray irradiation device (X-ray generator) 130. The X-ray detector 110 and the X-ray irradiation device 130 are arranged on both ends of an arm 100 so as to face each other. The X-ray detector 110 and the X-ray irradiation device 130 arranged on both ends of the arm 100 are provided so as to be rotatable around an object P, along two axes including an arm string and an axis perpendicular to the arm string, under the control of a drive controller which is not illustrated.

Upon reception of high voltage power supply from a high-voltage power supply 120, the X-ray irradiation device (X-ray generator) 130 generates X-rays in accordance with a condition of the high voltage power. The X-ray detector 110 includes a flat panel detector (FPD) and an analog to digital (A/D) conversion circuit (not illustrated). The FPD has a plurality of detection elements arrayed in two dimensions. In the FPD, scanning lines and signal lines are provided orthogonal to each other in between each of the detection elements. A grid (not illustrated) may be provided in front of the FPD. The grid is formed by alternately arranging grid plates and materials, such as aluminum and wood, to absorb scattered beams incident on the FPD and to thereby enhance contrast of X-ray images, the grid plates being formed from lead and the like which are high in X-ray absorbent, the materials easily transmitting X-rays. The A/D conversion circuit converts projection data made of serial analog signals (video signals) output from the FPD into digital signals, and outputs the digital signals to the operation control apparatus 20.

The X-ray detector 110 may be an image intensifier (II)-TV system. The II-TV system converts an X-ray which passed the object P and an X-ray directly incident on the system into visible light. The II-TV system then doubles the brightness in process of light-electron-light conversion to form highly sensitive projection data, and converts the optical projection data into electrical signals with use of a charge coupled device (CCD) image sensor.

The high-voltage power supply 120 can supply high voltage power to an X-ray tube of the X-ray irradiation device 130 under the control of the operation control apparatus 20.

The bed device 140 is placed on a floor surface and supports a top plate. The bed device 140 moves the top plate on which the object P is laid by using a bed driving device, which is not illustrated, under the control of the operation control apparatus 20.

An injector 150 controls a syringe used for administering a contrast medium to the object P. The injector 150 administers the contrast medium to the object P under the control of the operation control apparatus 20, and also controls so that the object P is irradiated with X-rays after a lapse of a specified time from administration of the contrast medium to the object P. Instead of using the injector 150, a user may manually administer the contrast medium and control start of X-ray irradiation.

A description is now given of the operation control apparatus 20. The operation control apparatus 20 is configured to include a communication controller 210, a memory circuitry 220, a main controller 230 including a processing circuitry, an input device 240, and a display 250.

The communication controller 210 implements various communication protocols corresponding to the configuration of an electronic network. Here, the electronic network refers to an entire information communication network using electric communication techniques. The electronic network includes hospital-based LANs, wireless/wired LANs, the Internet network, as well as telephonic communication line networks, optical fiber communication networks, cable communication networks, and satellite communication networks. The communication controller 210 acquires image data from the imaging apparatus 10 or from such a system as a Picture Archiving and Communication Systems (PACS), which is not illustrated, via the electronic network. Angiographic images may be generated by the processing circuitry of the main controller 230 executing a program stored in the memory circuitry 220 of the operation control apparatus 20, or may be generated and transmitted by an image processing apparatus and the like which are connected via the electronic network.

The memory circuitry 220 is configured to include a storage medium, such as a magnetic or optical recording medium, typically RAMs and ROMs, or a semiconductor memory. The storage medium is readable by a processing circuitry of the main controller 230. The memory circuitry 220 stores the image data collected by the imaging apparatus 10 and the like, and also stores a program for implementing various functions performed in the processing circuitry of the main controller 230. Part or entirety of the program and data in the storage medium may be downloaded through the electronic network. Such a program may execute generation of angiographic images and/or X-ray irradiation control.

The main controller 230 has a processing circuitry constituted by a CPU and the like. The processing circuitry loads the program stored in the memory circuitry 220 and also loads data necessary for executing the program to a RAM. The processing circuitry implements various functions in accordance with this program.

The processing circuitry of the main controller 230 may be constituted not by a CPU but by an integrated circuit such as an application specific integrated circuit (ASIC), a simple programmable logic device (SPLD), a complex programmable logic device (CPLD), and a field programmable gate array (FPGA), or an electronic circuit such as a micro processing unit (MPU).

The processing circuitry according to the present embodiment may be configured as a single circuit that implements all the functions, or may be a group of circuits each implements each function.

The input device 240 is constituted by a general input device, such as a keyboard, a touch panel, a ten key, and a mouse. The input device 240 outputs input signals corresponding to user actions, such as selection and input, to the main controller 230.

For example, the display 250 is constituted by a general display, such as a liquid crystal display and an organic light emitting diode (OLED) display. In addition, the display 250 displays angiographic images and the like under the control of the main controller 230.

Figure 2:
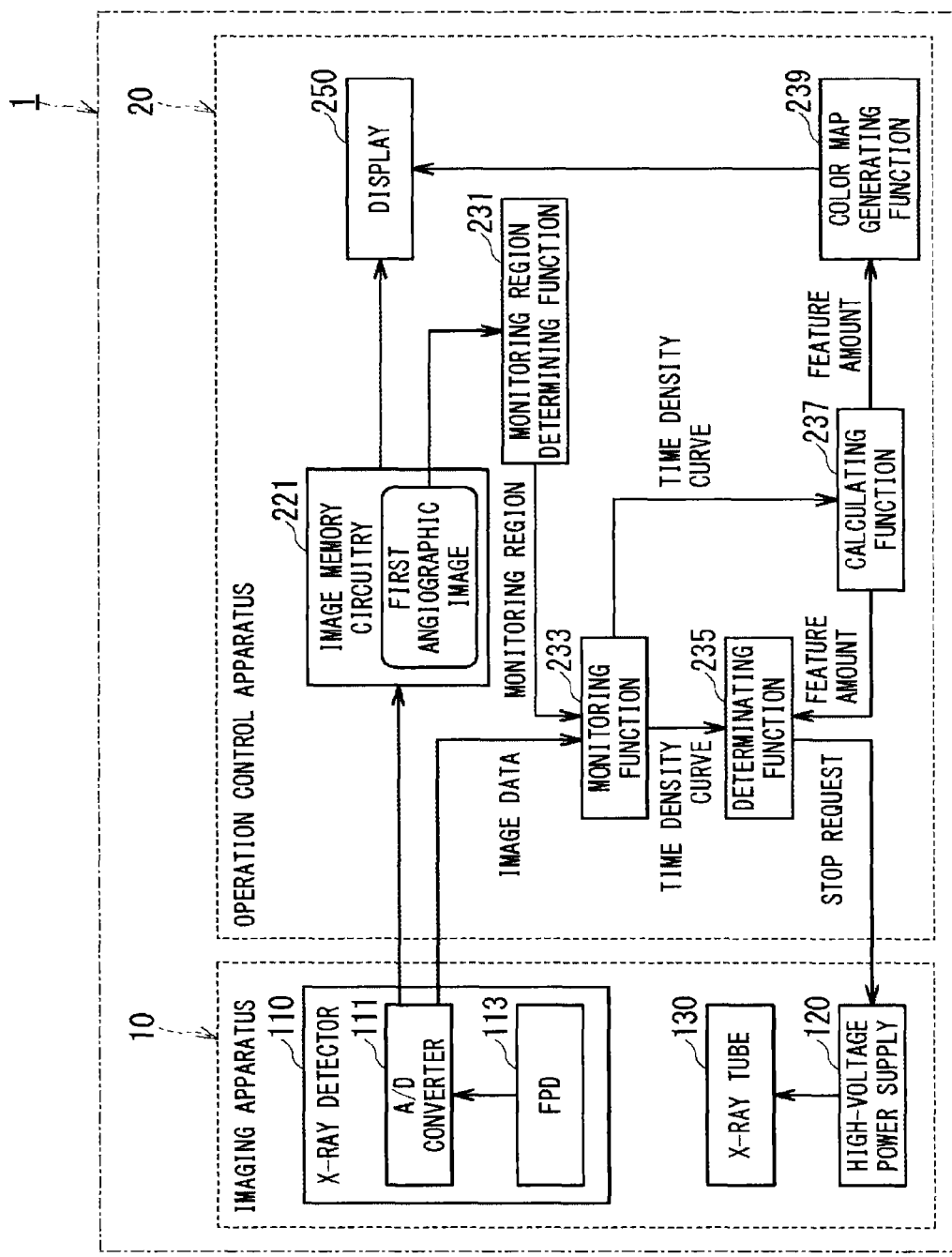
FIG. 2 is a functional block diagram illustrating a functional configuration example of the X-ray diagnostic apparatus 1 in the embodiment.

FIG. 2 is a functional block diagram illustrating a functional configuration example of the X-ray diagnostic apparatus 1 in the embodiment. As described in FIG. 1, the X-ray diagnostic apparatus 1 according to the embodiment is mainly constituted of the imaging apparatus 10 and the operation control apparatus 20. In the X-ray diagnostic apparatus 1 according to the embodiment, the operation control apparatus 20 controls X-ray irradiation when second angiographic images are acquired based on first angiographic images of the object P imaged by the imaging apparatus 10.

Hereinafter, in the description with reference to FIG. 1 through FIG. 8, angiographic images before performing treatment, such as revascularization, on an object are referred to as first angiographic images, and angiographic images after performing treatment are referred to as second angiographic images.

As illustrated in FIG. 2, the operation control apparatus 20 includes an image memory circuitry 221, a monitoring region determining function 231, a monitoring function 233, a determining function 235, a calculating function 237, a color map generating function 239, and a display 250. The monitoring region determining function 231, the monitoring function 233, the determining function 235, the calculating function 237, and the color map generating function 239 are functions implemented when the program stored in the memory circuitry 220 is executed by the processing circuitry of the main controller 230. The term "function" means a kind of computer program.

The image memory circuitry 221 stores the first angiographic images which are difference images between a mask image before administration of the contrast medium to the object and contrast images after administration of the contrast medium to the object. The first angiographic images may be data generated in external apparatuses connected via the electronic network, such as the PACS and image processing apparatuses, or may be data generated in the color map generating function 239 of the operation control apparatus 20 based on the image data acquired by the imaging apparatus 10.

The monitoring region determining function 231 determines a monitoring region, which is to be observed when acquiring the second angiographic images, based on the first angiographic images. The monitoring region is determined based on the first angiographic images acquired before treatment and displayed on the display 250. The monitoring region is determined when a user, such as a doctor, specifies a region of interest (ROI) in a first angiographic image displayed on the display 250. Methods for determining the monitoring region will be described later.

The monitoring function 233 monitors change in signal strength of each of pixels included in the monitoring region of a contrast image that is the second angiographic image. The monitoring function 233 generates a TDC based on successive change in signal strength of each of the pixels in the contrast image acquired after administration of the contrast medium in the imaging apparatus 10. Since the contrast medium administered to the object absorbs X-rays, the signal strength of each of the pixels in the contrast images deteriorates. The TDC is a graph plotting a blood concentration of the contrast medium based on successive change in the signal strength of each of the pixels. The X-ray diagnostic apparatus 1 according to the present embodiment monitors each of the pixels contained in the monitoring region with the TDC so as to determine the timing of changing an X-ray condition (timing of starting to reduce an X-ray dose or timing of stopping X-ray irradiation) by controlling the X-ray irradiation device 130 to reduce a radiation dose, and to thereby avoid unnecessary exposure. When the X-ray irradiation is stopped, unnecessary exposure can considerably be reduced. When the X-ray dose is reduced, it becomes possible to continuously referring to perspective images of the object while reducing unnecessary exposure. The TDC generated in the monitoring function 233 will be described later.

Based on whether or not the signal strength of each of the pixels contained in the monitoring region satisfies a specified condition, the determining function 235 determines whether or not to change the X-ray condition (to reduce an X-ray dose or to stop X-ray irradiation) in imaging of the second angiographic images which is sequentially performed. Based on the TDC generated for each of the pixels in the monitoring function 233, the determining function 235 determines that the condition is satisfied when, for example, a contrast medium concentration in blood is lowered by a specified percentage from the concentration at time to peak (TP), the TP being the time when the concentration becomes a maximum. The determining function 235 defines a physical value calculable from the TDC such as the concentration at TP as a feature amount (hereinafter simply referred to as a feature amount), and performs determination based on the feature amount for all the pixels set as monitoring targets in the monitoring region. The determining function 235 transmits a request to change the X-ray condition (a request to reduce an X-ray dose or a request to stop X-ray irradiation) to the imaging apparatus 10, when all the pixels set as monitoring targets satisfy the condition. Methods for determination in the determining function 235 will be described later. The following description describes the case where the change of the X-ray condition is to stop X-ray irradiation.

The calculating function 237 calculates at least one feature amount out of a maximum concentration value, a half-width concentration value that is a half width of the TDC, mean transit time of the contrast medium, a lower area of the TDC, a blood flow velocity of the object obtained from the TDC, a blood flow rate of the object obtained from the TDC, arrival time of the contrast medium at each pixel based on the TDC, TP, and a gradient to the maximum concentration value in the TDC. Such feature amounts are calculated based on the TDC generated in the monitoring function 233 by methods described in JP-A 2014-12133 and the like. The blood flow velocity and the like are calculated by commonly used methods, such as a method of concentration at half maximum and a method of maximum concentration gradient.

The color map generating function 239 generates a color map (colored parametric image) in which colors corresponding to values of the feature amounts are allocated to each of the pixels in the second angiographic image. An image in which parameters other than an X-ray transmissivity are visualized by such color mapping is a parametric image (hereinafter referred to as a PI image) obtained by what is called parametric imaging.

The parametric imaging herein refers to, for example, a process of generating a PI image in which one or more parameters are visualized in color or gray scales. The calculating function 237 calculates a parameter value of each pixel for generating the PI image based on time change in pixel value of each pixel corresponding to an identical region of the object in a plurality of DA images or a plurality of DSA images acquired continuously and sequentially in a time series. The following description discusses an example in which the color map generating function 239 generates the PI image as a color image (color map).

The color map generating function 239 is configured to be able to generate mask images, contrast images, and difference images based on the image data acquired by the imaging apparatus 10.

The display 250 displays the first angiographic images, the second angiographic images, and the PI images generated by the color map generating function 239.

(2) Operation

Figure 3:
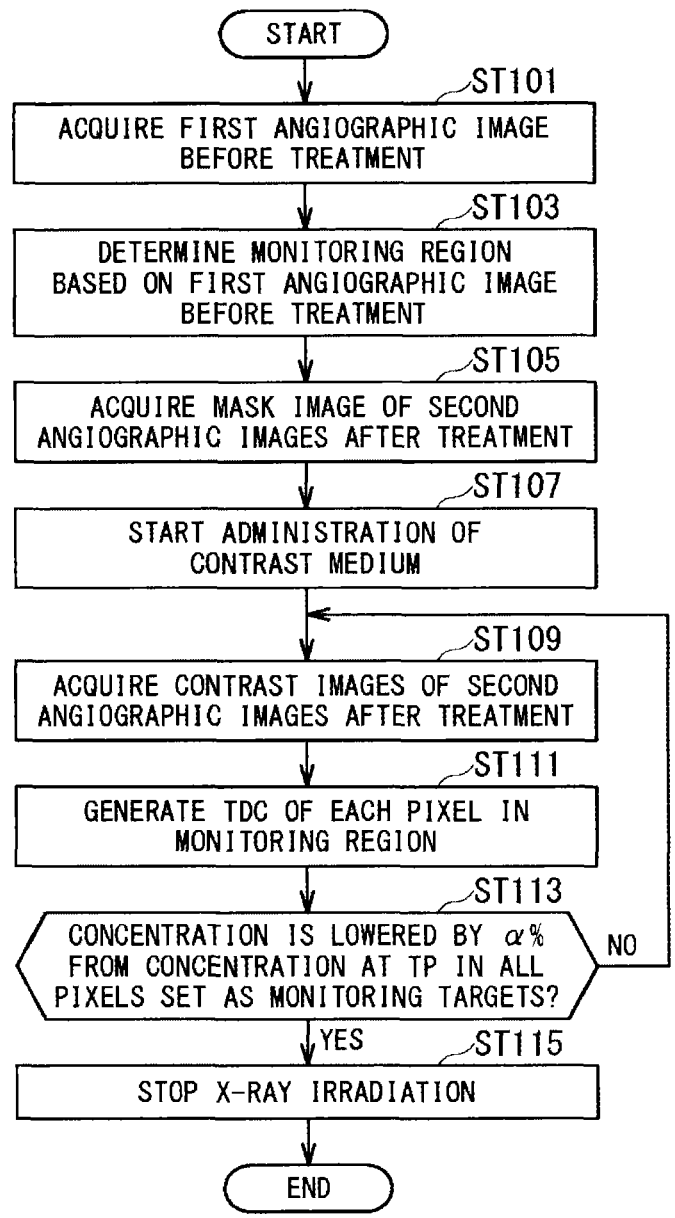
FIG. 3 is a flow chart illustrating one example of operation of the X-ray diagnostic apparatus 1 in the embodiment.

FIG. 3 is a flow chart illustrating one example of operation of the X-ray diagnostic apparatus 1 in the embodiment. FIG. 3 illustrates an example in which the change of the X-ray condition is to stop X-ray irradiation.

In ST101, the image memory circuitry 221 acquires first angiographic images before treatment. As the first angiographic images, the data acquired from the PACS and/or the image processing apparatus, which is connected to the X-ray diagnostic apparatus 1 via the electronic network, may be stored, or the data generated in the operation control apparatus 20 of the X-ray diagnostic apparatus 1 may be stored.

In ST103, the monitoring region determining function 231 determines a monitoring region based on the first angiographic images before treatment. The monitoring region is determined by a user such as a doctor, who inputs an ROI in a first angiographic image displayed on the display 250 through the input device 240 and the like.

Hereinafter, methods for determining the monitoring region will be described with reference to FIGS. 4 and 5. The description is given based on an example of angiographic images acquired in the case of treating an aneurysm with a catheter and the like and restoring blood circulation of a blood vessel ahead of the aneurysm.

Figure 4A:
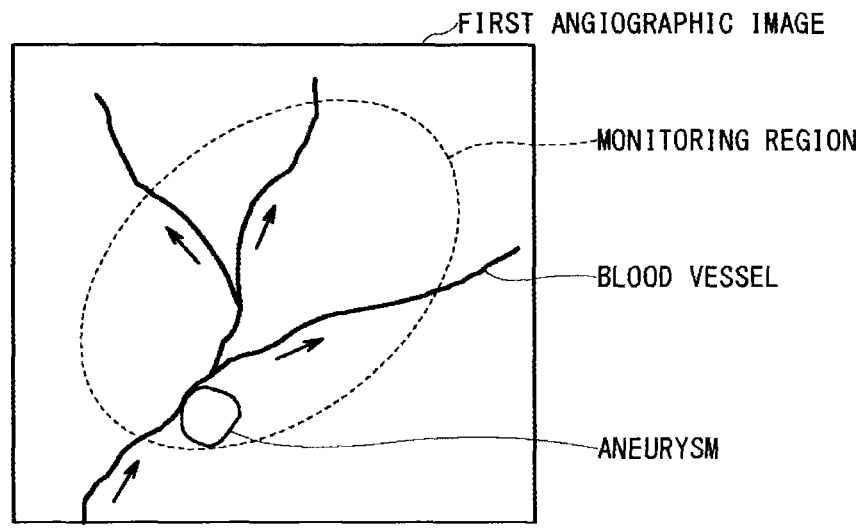
FIGS. 4A and 4B illustrate first and second methods for determining the monitoring region in the X-ray diagnostic apparatus 1 according to the embodiment.
Figure 4B:
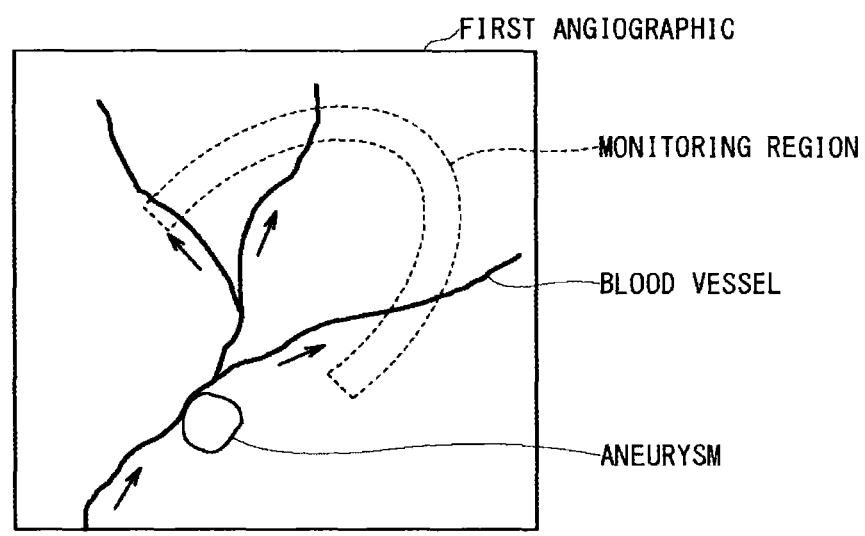

FIGS. 4A and 4B illustrate first and second methods for determining the monitoring region in the X-ray diagnostic apparatus 1 according to the embodiment.

FIG. 4A illustrates an example of the first method for determining the monitoring region. In the example of the first determination method, an oval region is determined as a monitoring region. The monitoring region is determined by setting an ROI in the first angiographic image illustrated in FIG. 4A. For example, in FIG. 4A, when an oval region encircled with a dashed line is set as an ROI on the screen, the set ROI is determined as the monitoring region. The oval region illustrated in FIG. 4A contains all articles shown in the first angiographic image, including an aneurysm and a blood vessel branched into three blood vessels. Arrows shown in the first angiographic image represent blood flow directions. Blood circulation of the blood vessel ahead of the aneurysm is predicted to be changed by executing of treatment. Thus, in the first determination method of FIG. 4A, the monitoring region is determined by encircling a region, which contains the blood vessel influenced by treatment, with a closed curve so as to ascertain the effect of treating the aneurysm through observation of hemodynamics after treatment. Although an oval region is specified in FIG. 4A, a specified region may be in other shapes such as a circular, rectangular, or polygonal shape.

FIG. 4B illustrates an example of the second method for determining the monitoring region. Although the ROI specified with a closed curve is determined as the first monitoring region, a belt-like line with a prescribed width is determined as the monitoring region in the second determination method. In the case of the belt-like monitoring region illustrated in FIG. 4B, a belt-like ROI may be input in the first angiographic image, so that the region specified as the ROI is determined as the monitoring region. Or alternatively, an arc-like line may be input as the ROI, so that a prescribed region, spreading like a belt with the line which is input as the ROI being used as a center or as a boundary line, is determined as the monitoring region. Although the arc-like monitoring region is illustrated in FIG. 4B, linear or other curved regions may be determined as the monitoring region.

Figure 5A:
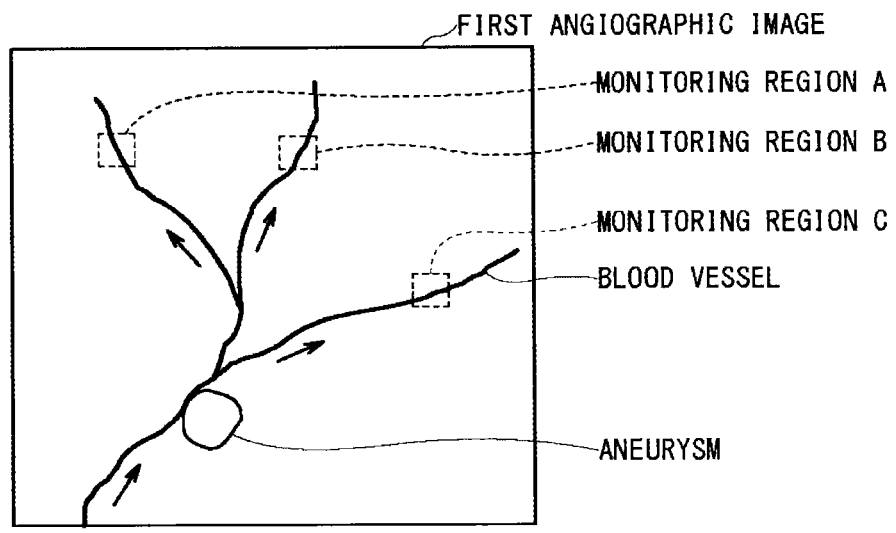
FIGS. 5A and 5B illustrate third and fourth methods for determining the monitoring region in the X-ray diagnostic apparatus 1 according to the embodiment.
Figure 5B:
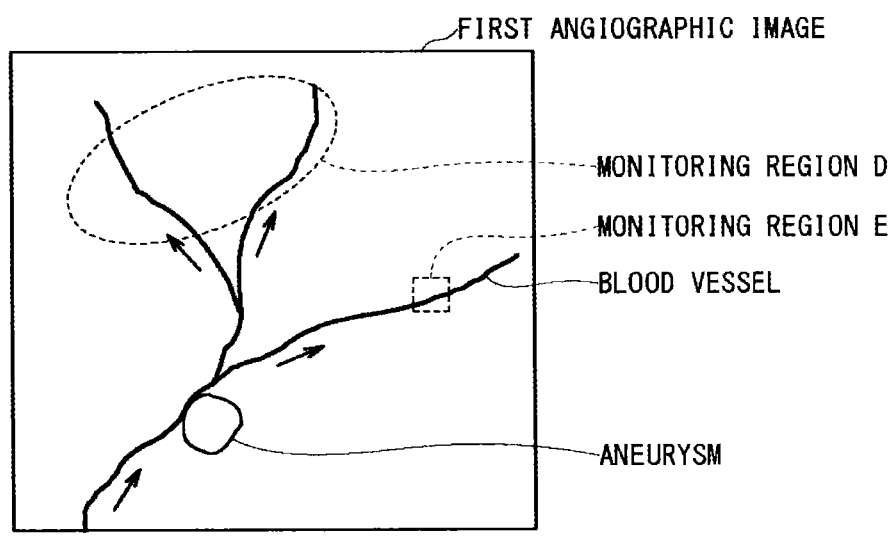

FIGS. 5A and 5B illustrate third and fourth methods for determining the monitoring region in the X-ray diagnostic apparatus 1 according to the embodiment.

FIG. 5A illustrates an example of the third method for determining the monitoring region. In FIG. 5A, the monitoring region is determined by specifying a blood vessel that the user, such as a doctor, wants to observe to ascertain the effect of treating the aneurysm. In FIG. 5A, the monitoring region is determined based on positions each specified as an ROI. The user specifies the ROI by displaying a cursor and/or a pointer or by click or touch operation on the first angiographic image displayed on the display 250 through the input device 240 which includes a mouse and the like. A given region around the position (coordinates) on the first vascular imaging specified by user's click operation or the like may be determined as the monitoring region, or the cursor and/or the pointer may have a prescribed size. Although a rectangular monitoring region expressed by a dashed line is illustrated in FIG. 5A, the monitoring region may be in other forms such as a circle and an oval. In the example of FIG. 5A, a monitoring region A, a monitoring region B, and a monitoring region C are shown for each of three branched blood vessels in the first angiographic image. All the blood vessels displayed on the first angiographic image may be specified, or part of the blood vessels may be specified.

FIG. 5B illustrates an example of the fourth method for determining the monitoring region. In the example of FIG. 5B, the first and third methods for determining the monitoring region are combined. The first method is to specify a prescribed range containing a plurality of blood vessels, while the third method is to specify one blood vessel. By such combination, the methods for determining the monitoring region can be changed in accordance with the form and/or position of blood vessels, priority of observation targets, and the like. This makes it possible to achieve precise determination of the monitoring target. For example, in FIG. 5B, an oval monitoring region D illustrated on the upper side specifies a plurality of blood vessels, and a rectangular monitoring region E illustrated on the lower side specifies one blood vessel. Thus, the methods for specifying the monitoring region may be selected in accordance with the shape of a branched blood vessel, the density of a blood vessel, or the like. When an organ is present ahead of a branched blood vessel, the vessel may be observed to know whether a nutrient vessel of the organ is functioning. Blood vessels which are anatomically in close relation with a treatment area may be specified in a wide range (for example by the first determination method). Less important blood vessels may be specified as a point (for example by the third determination method).

Thus, the methods for specifying the monitoring region may be selected depending on the purpose of ascertaining the effect of treatment, and/or the priority thereof. Narrowing down the monitoring target by selecting a necessary portion and setting it as the monitoring region can reduce calculation amounts.

Although the methods for determining the monitoring region have been described with examples, the methods are not limited thereto. A treatment target portion (an aneurysm in the examples of FIGS. 4 and 5) may be specified, and a prescribed range around the specified portion may be set as the monitoring region. Or a position in a given distance from the specified portion may be determined as the monitoring region.

After the monitoring region is determined based on the first angiographic images before treatment (ST103), angiographic images after treatment (second angiographic images) are acquired. A description is now given of acquisition of the second angiographic images with reference again to the flow chart of FIG. 3. In this example, the determining function 235 performs determination based on Time to Peak (TP) as a feature amount, the TP being the time when the contrast medium concentration in blood becomes a maximum. In ST105, the imaging apparatus 10 images at least one mask image of the second angiographic images after treatment. In the case of the second angiographic images after treatment, the mask image before administration of the contrast medium is acquired as in the case of imaging the first angiographic images.

In ST107, the injector 150 of the imaging apparatus 10 starts administration of the contrast medium to the object.

In ST109, the imaging apparatus 10 images contrast images of the second angiographic images after treatment.

In ST111, the monitoring function 233 generates a TDC of each pixel of the monitoring region in the contrast image.

In ST113, the determining function 235 determines whether or not to transmit a request to stop X-ray irradiation to the imaging apparatus 10, based on whether or not a condition of the contrast medium concentration is lowered by a % from the concentration at TP is satisfied in all the pixels of the monitoring region. When the condition is satisfied (Yes), a signal to stop X-ray irradiation is transmitted to the imaging apparatus 10 in ST115, and a voltage supply to the X-ray irradiation device 130 from the high-voltage power supply 120 is stopped. When the condition is not satisfied (NO), contrast images are newly acquired in ST109, and TDCs are generated for the contrast images acquired in ST111. In imaging of the contrast images, an X-ray is emitted like a pulse at constant intervals, and a plurality of contrast images are successively acquired. Whenever the contrast images are acquired, the monitoring function 233 generates a TDC of each of the pixels contained in the monitoring region.

Figure 6A:
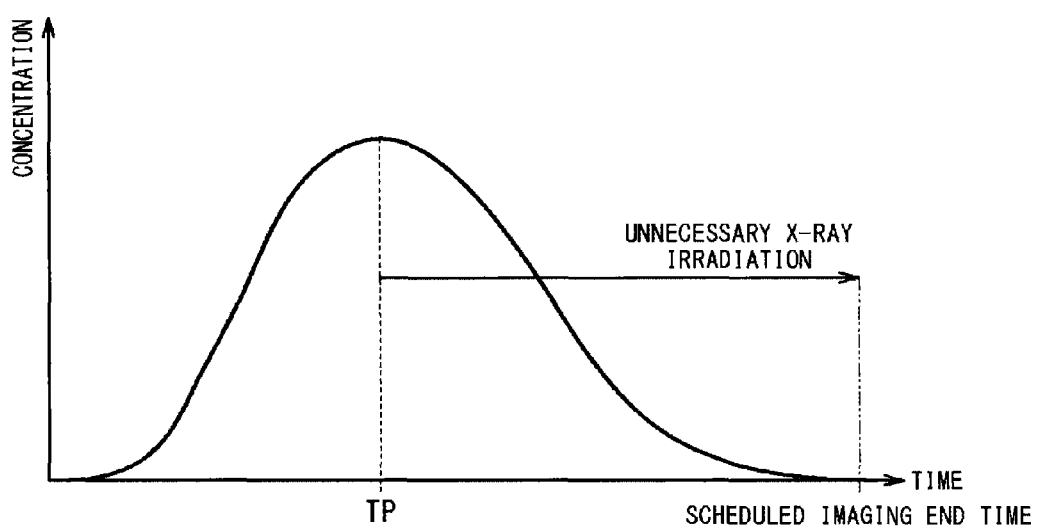
FIGS. 6A and 6B illustrate TDCs of the X-ray diagnostic apparatus 1 according to the embodiment.
Figure 6B:
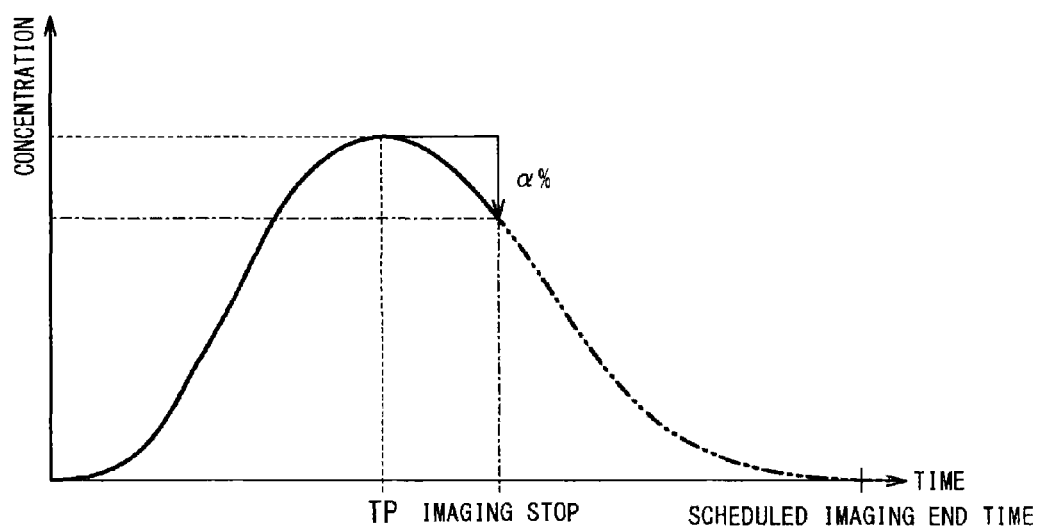

FIGS. 6A and 6B illustrate TDCs of the X-ray diagnostic apparatus 1 according to the embodiment. In FIG. 6A, a certain pixel on the blood vessel contained in the region specified as the monitoring region is taken as an example. When the contrast medium is administered to the patient, the concentration of the contrast medium in the blood of the object starts to rise. After reaching a maximum concentration, the concentration decreases, and the contrast medium is completely washed out in the end. Therefore, when the concentration of the contrast medium in the blood is successively monitored, the concentration is expressed as a mountain-like graph having a peak at Time to Peak (TP), which is the time when the concentration of the contrast medium in the blood becomes a maximum, as illustrated in FIG. 6A. In general imaging of angiographic images, as illustrated in FIG. 6A, imaging is performed during a period of time from the start of rise in concentration of the contrast medium to scheduled imaging end time when the contrast medium is observed to be completely washed out. However, in the case of observing the form of a blood vessel, an angiographic image can be generated at TP when the blood vessel is sufficiently contrasted. Therefore, in the case where imaging is performed for the purpose of acquiring angiographic images at TP, X-ray irradiation is unnecessary during a period of time expressed by an arrow, that is, from TP to the scheduled imaging end time.

Accordingly, in the present embodiment, in the case of, for example, generating an angiographic image at TP as illustrated in FIG. 6B, the X-ray condition is changed (e.g., X-ray irradiation is stopped) on condition that the concentration reaches TP. To determine that the concentration reaches TP, the condition that the concentration of the contrast medium is lowered by a prescribed percentage (for example, α% in FIG. 6B) from the maximum concentration is used as a determination criterion. The feature amounts in the TDC are selected in accordance with the purpose of acquiring the angiographic image, the purpose of observation, and the like. With the selected feature amount as a determination criterion, X-ray exposure is stopped prior to an original scheduled imaging end time, or the X-ray dose is decreased to reduce X-ray exposure.

In the TDC illustrated in FIG. 6, one mountain-like peak of the concentration plotted by rise and fall of the concentration is present. However, a plurality of blood vessels may overlap in one pixel, and in such a case, the contrast media in the plurality of blood vessels reach their peaks at times different from each other. As a result, a plurality of peaks are present in the TDC. When a blood vessel has abnormality, a curve is not as illustrated in FIG. 6A in some cases. Even in such cases, as illustrated in FIG. 6B, X-ray irradiation time can be reduced by performing determination on the basis that the concentration is lowered by a certain percentage from the observed feature amount (such as TP).

Figure 7:
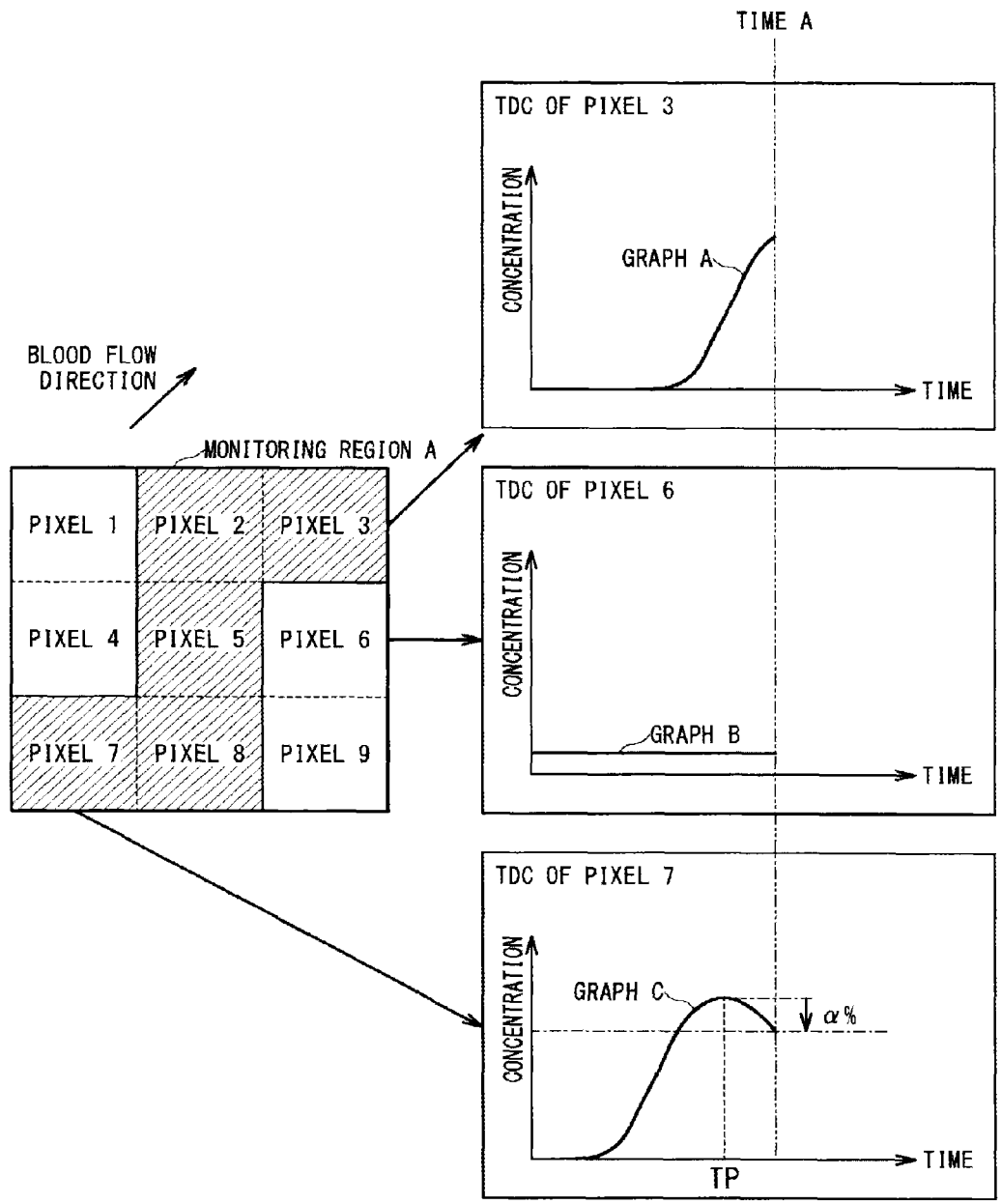
FIG. 7 illustrates an example of the TDC of each pixel at time A.
Figure 8:
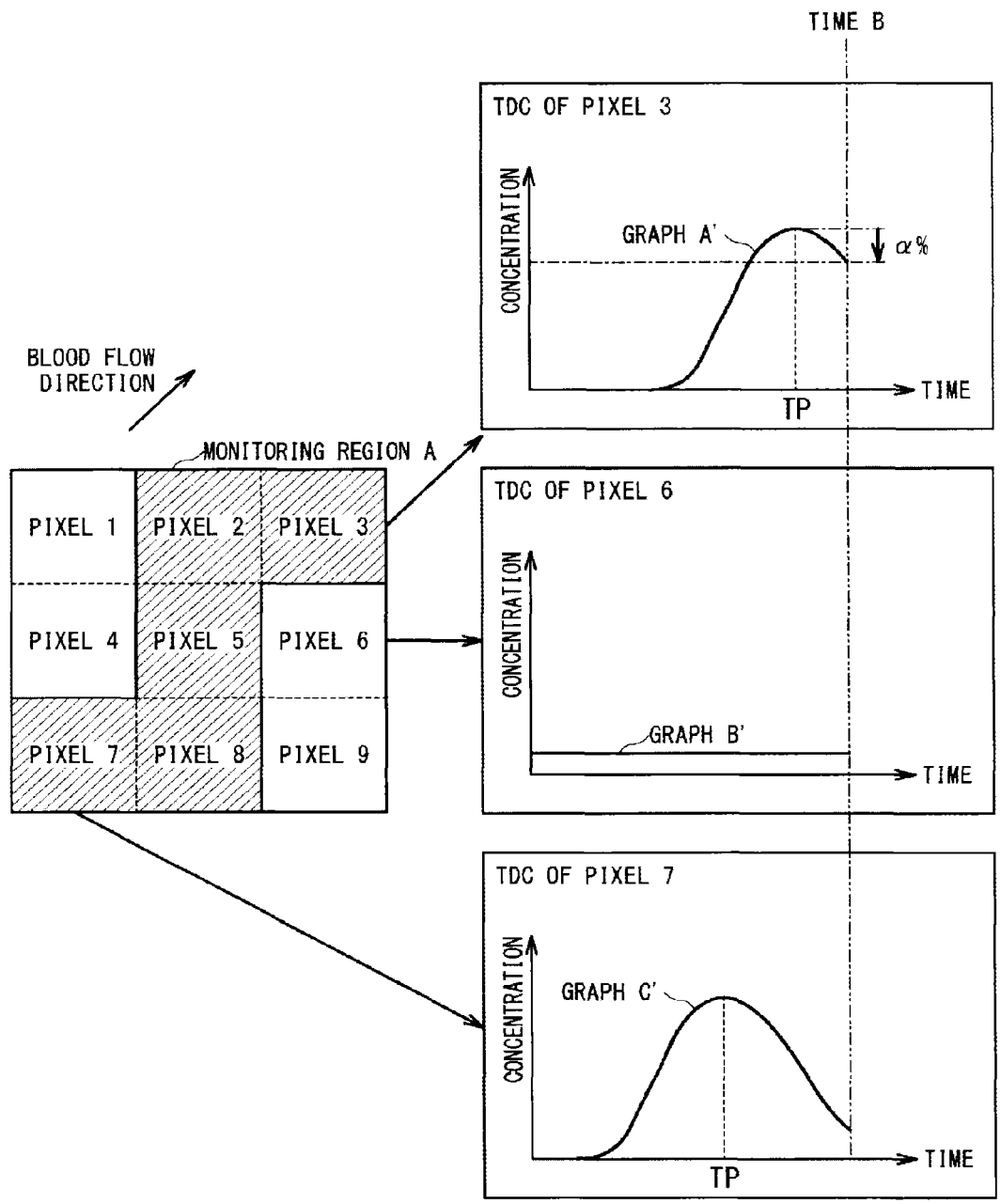
FIG. 8 illustrates an example of the TDC of each pixel at time B after a lapse of definite period of time from the time A of FIG. 7.

Hereinafter, determination methods in the determining function 235 will be described in FIGS. 7 and 8. FIG. 7 illustrates an example of the TDC of each pixel at time A. FIG. 8 illustrates an example of the TDC of each pixel at time B after a lapse of definite period of time from the time A of FIG. 7.

FIG. 7 is a first view describing the determination method in the determining function 235 of the X-ray diagnostic apparatus 1 according to the embodiment. FIG. 7 illustrates examples of TDCs of respective pixels at time A. An ordinate of each TDC represents the concentration of the contrast medium in the blood calculated from the X-ray transmissivity of the contrast image, while an abscissa represents elapsed time after administration of the contrast medium by the injector 150 and the like.

A left-hand side of FIG. 7 illustrates the case where nine pixels from a pixel 1 to a pixel 9 are contained in the monitoring region A illustrated in FIG. 5A. In the example of FIG. 7A, among nine pixels, five shaded pixels including pixels 2, 3, 5, 7, and 8 represent blood vessel signals. An arrow illustrated on the upper left side of a monitoring region A on the left-hand side of FIG. 7 represents a blood flow direction. Therefore, in the monitoring region A on the left-hand side of FIG. 7, the contrast medium flows in a direction from the pixel 7 to the pixel 3.

Illustrated on the right-hand side of FIG. 7 are a TDC (graph A) of the pixel 3, a TDC (graph B) of the pixel 6, and a TDC (graph C) of the pixel 7 in order from the top.

Since the pixel 6 is not a pixel representing a blood vessel, the graph B depicts an example free from an influence of the contrast medium. Accordingly, a large change does not occur in the graph B as time passes. Since pixels (hereinafter referred to as background pixels) other than such pixels representative of a blood vessel are also contained in the monitoring region, the monitoring function 233 may exclude the background pixels from the monitoring target. The determining function 235 may determine that the condition is satisfied in all the pixels excluding the background pixels. As for the background pixels, determination can be made on condition that the concentration in the TDC is equal to or less than a given threshold value, or a difference between a maximum value and a minimum value is small at a certain point of time. The monitoring function 233 may sample the pixels representative of a blood vessel contained in the monitoring region and sets part of the sampled pixels as a monitoring target so as to enhance its calculation ability.

The pixels 3 and 7 are pixels on the blood vessel. Since blood flows in the direction from the pixel 7 to the pixel 3, the contrast medium flows in the direction from the pixel 7 to the pixel 3. Therefore, as illustrated in the graphs C and A, TP is observed in the graph C of the pixel 7 at time A, whereas TP is not observed in the graph A of the pixel 3, indicating that the concentration is in the middle of rising.

For example, when the determining function 235 makes determination on condition that the concentration is lowered by α% from TP, the determining function 235 determines that the pixel 7 satisfies the condition based on the TDC in the graph C, but determines that the pixel 3 does not satisfy the condition based on the graph A. Therefore, since not all the pixels of the monitoring target satisfy the condition, the determining function 235 determines to continue X-ray irradiation (No in ST113).

FIG. 8 is a second view describing the determination method in the determining function 235 of the X-ray diagnostic apparatus 1 according to the embodiment. The left-hand side of FIG. 8 is similar to the left-hand side of FIG. 7. The right-hand side of FIG. 8 illustrates TDCs of the pixels 3, 6, and 7 at time B, respectively. A TDC (graph A') of the pixel 3, a TDC (graph B') of the pixel 6, and a TDC (graph C') of the pixel 7 are illustrated in order from the top.

Since the pixel 6 is not a pixel on the blood vessel as illustrated in FIG. 7, change in contrast medium concentration is not observed.

The pixels 3 and 7 are pixels on the blood vessel, and the contrast medium flows in the direction from the pixel 7 to the pixel 3 as described in FIG. 7. Illustrated on the right-hand side of FIG. 8 are TDCs of the pixels 7 and 3 at time B after a lapse of definite period of time from the time A of FIG. 7. In graph C' of FIG. 8, the concentration of the contrast medium is lowered by α% from the concentration at TP and then is further lowered. In the graph A' of FIG. 8, the concentration of the pixel 3 reaches TP and is then lowered by α% from the concentration at TP.

For example, when the determining function 235 makes determination on condition that the concentration is lowered by a % from TP, the determining function 235 determines that the pixel 3 satisfies the condition at time B. Although not illustrated, when the condition is satisfied in other pixels (pixels 2, 5, and 8), the determining function 235 determines that all the pixels of the monitoring region A satisfy the condition. Determination is similarly performed with respect to other monitoring regions in FIG. 5A. When it is determined that the condition is satisfied in all the monitoring regions, a request to stop X-ray irradiation is transmitted to the imaging apparatus 10 (Yes in ST113).

Thus, the X-ray diagnostic apparatus 1 according to the present embodiment generates TDCs based on the signal strength of the pixels in image data. At the moment when necessary image data is acquired based on the TDCs, the X-ray diagnostic apparatus 1 stops X-ray irradiation or reduces the X-ray dose before the preset scheduled imaging end time. The preset scheduled imaging end time is set with a margin in most of the cases. In some cases, imaging is continued even after the contrast medium is washed out. In this way, unnecessary images are acquired depending on the purpose of examination in the conventional imaging method. In the X-ray diagnostic apparatus 1 according to the present embodiment, X-ray irradiation can be stopped, or the X-ray dose can be reduced at the moment when necessary images are acquired. This makes it possible to avoid unnecessary exposure and to carry out efficient imaging. Since unnecessary image data is not acquired, the X-ray diagnostic apparatus 1 can also contribute to reduction in data volume.

Although the examples in which the determining function 235 uses TP as a feature amount have been described, the present invention is not limited to these examples. Other physical values calculable from the TDC may also be used as a feature amount. For example, determination to stop X-ray irradiation may be made, based on at least one of the feature amounts on condition that the specified feature amount can be acquired. The feature amounts calculated by the calculating function 237 include a half-width concentration value used as the half width in a TDC, mean transit time of the contrast medium, a lower area of the TDC, a blood flow velocity of the object obtained from the TDC, a blood flow rate of the object obtained from the TDC, arrival time of the contrast medium at each pixel based on the TDC, TP, and a gradient to a maximum concentration value in the TDC. For example, in the case of the half-width concentration value, determination may be made on condition that the concentration is lowered by a specified value from the half-width concentration value. In the case of the mean transit time of the contrast medium, determination may be made by setting a specified threshold, or may be made on condition that calculated mean transit time becomes constant (difference between sequential contrast images acquired in time series became less than a specified percentage). The condition may be set depending on the properties of the feature amount to be used.

Thus, by setting the feature amount to observe, the user can reduce the X-ray dose or can stop X-ray irradiation at the moment when the number of images necessary for calculating the feature amount can be acquired. The color map generating function 239 generates a PI image wherein colors are assigned in accordance with acquired values of the feature amount.

In the aforementioned embodiment, the example of reducing the X-ray dose in imaging of the second angiographic images acquired after treatment have been described. Hereinafter, a modified example for reducing the dose of X-ray irradiation in the entire angiographic examination is described. In the modified example, prior to main imaging performed for acquiring images used for actual diagnosis, an angiographic image is acquired with a low dose as compared with the main imaging. A first angiographic image in the modified example illustrated in FIG. 9 is acquired by imaging which is performed prior to main imaging with a low dose as compared with the main imaging.

Figure 9A:
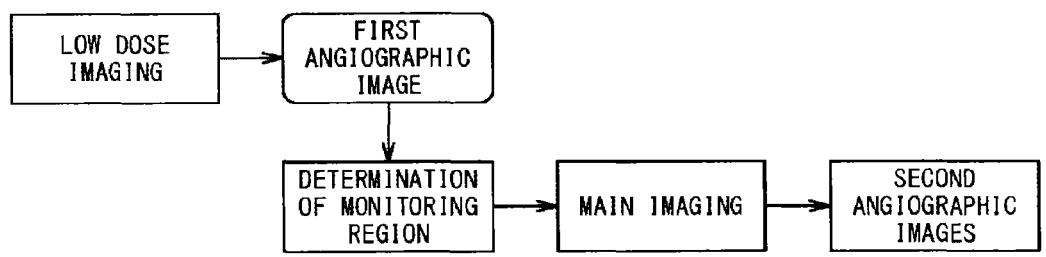
FIG. 9A illustrates an example of the imaging procedure in the case where imaging of angiographic images is performed once as main imaging.
Figure 9B:
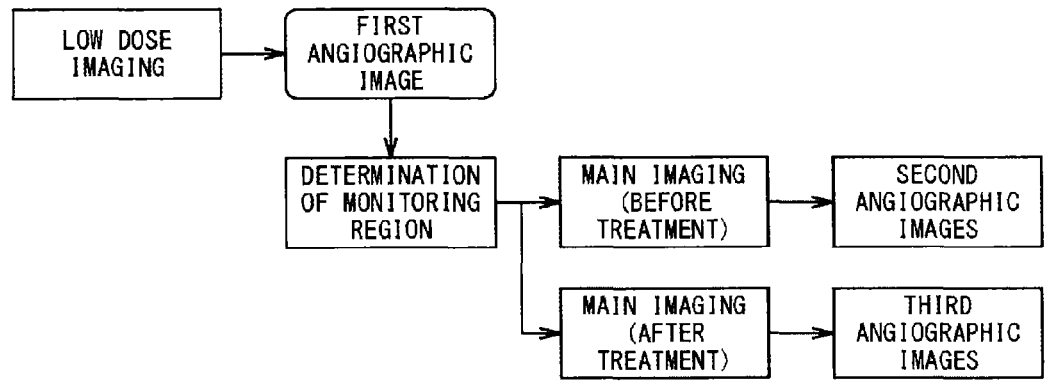
FIG. 9B illustrates an example of the imaging procedure in the case where the timing to stop X-ray irradiation is determined in the main imaging performed both before and after treatment as described in the embodiment.

FIGS. 9A and 9B illustrate imaging procedures in the modified example of the X-ray diagnostic apparatus 1 according to the embodiment.

FIG. 9A illustrates an example of the imaging procedure in the case where imaging of angiographic images is performed once as main imaging. In "low dose imaging" on the upper left side of FIG. 9A, imaging is performed prior to main imaging to acquire an angiographic image with a low dose as compared with the main imaging. Based on the acquired "first angiographic image", "determination of monitoring region" is performed. The monitoring region can be specified when placement of blood vessels can be recognized in the image. Even if the image taken with a low dose includes noise and the like, the monitoring region can still sufficiently be specified.... Once the monitoring region is determined based on the first angiographic image acquired by low dose imaging, "main imaging" is performed. In main imaging, the monitoring function 233 generates a TDC for each of the pixels in the specified monitoring region. The determining function 235 determines the timing of changing the X-ray condition (timing of starting to reduce the X-ray dose or timing of stopping X-ray irradiation) by controlling the X-ray irradiation device 130 so as to reduce the radiation dose based on the TDC. By performing determination in the determining function 235, imaging with a high dose, which is necessary for PI image generation, can be ended before the scheduled imaging end time. As a result, the X-ray radiation dose in the entire examination can be reduced. The following description discusses the case where the change of the X-ray condition is to stop X-ray irradiation.

In FIG. 9B, as in FIG. 9A, "determination of monitoring region" is performed in advance by "low dose imaging". In the example of FIG. 9B, the timing to stop X-ray irradiation is determined in the main imaging performed both before and after treatment as described in the embodiment. Specifically, even "before treatment (main imaging)", the monitoring region is determined and the timing to stop X-ray irradiation is controlled in imaging of "second angiographic image" based on the first angiographic image acquired by low dose imaging. Next, even "after treatment (main imaging)", the monitoring region is determined, imaging of "third angiographic image" is performed, and X-ray irradiation timing is controlled based on the first angiographic image acquired by low dose imaging. The monitoring region in the main imaging after treatment may be determined based on the second angiographic image as in the aforementioned embodiment.

The first angiographic image acquired by low dose imaging may be an image which can show placement of blood vessels for determination of the monitoring region. Therefore, it is sufficient to acquire at least one contrast image of the first angiographic image before and after arrival of the contrast medium at the blood vessel as an imaging target after administration of the contrast medium. Imaging can also be performed with a reduced amount of the contrast medium as compared with typical imaging of angiographic images. In this way, low dose imaging can be executed with a radiation dose considerably smaller than that in the main imaging.

Therefore, it becomes possible to reduce the X-ray radiation dose of the entire angiographic examination by acquiring an angiographic image with a low dose in advance to determine the monitoring region.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:
an X-ray generator configured to generate X-rays for irradiating an object; and
processing circuitry configured to
generate a plurality of contrast images sequentially based on the X-rays after administration of a contrast medium to the object,
determine a monitoring region in the plurality of contrast images,
monitor change in signal strength of each of pixels included in the monitoring region of the plurality of contrast images sequentially generated,
determine whether or not the signal strength of each of the pixels included in the monitoring region satisfies a specified condition,
control the X-ray generator based on a result of the determination so as to reduce an X-ray dose or to turn off irradiation of the X-rays, and
generate a parametric image based on a feature amount determined by change in signal strength of each of pixels of a part of the plurality of contrast images sequentially generated, the part of the plurality of contrast images sequentially generated being generated before the X-ray generator is controlled based on the result of the determination.

2. The X-ray diagnostic apparatus according to claim 1, wherein
the processing circuitry sequentially generates a plurality of difference images between each of the plurality of contrast images sequentially generated and a mask image generated before the administration of the contrast medium to the object, and generates the parametric image based on the feature amount determined by change in signal strength of each of pixels of a part of the plurality of difference images sequentially generated, the part of the plurality of difference images sequentially generated being generated before the X-ray generator is controlled based on the result of the determination.

3. The X-ray diagnostic apparatus according to claim 1, wherein
the feature amount is time at which a peak in the change in signal strength appears.

4. The X-ray diagnostic apparatus according to claim 1, wherein
the processing circuitry determines a plurality of monitoring regions.

5. The X-ray diagnostic apparatus according to claim 1, wherein
the processing circuitry determines whether or not the signal strength of each of the pixels included in the monitoring region is lowered by a specified percentage from a peak.

6. The X-ray diagnostic apparatus according to claim 1, further comprising
a display to display the image generated by the processing circuitry, wherein
the processing circuitry determines, as the monitoring region, a region selected from the image displayed on the display as related to treatment of the object.

7. The X-ray diagnostic apparatus according to claim 1, wherein
the monitoring region is specified on the image generated by the processing circuitry such that the monitoring region has a prescribed range and encircled with a closed curve in a rectangular, circular, or oval shape.

8. The X-ray diagnostic apparatus according to claim 1, wherein
the monitoring region is specified on the image generated by the processing circuitry such that the monitoring region has a belt-like region expressed with a curved line or a straight line having a prescribed width.

9. The X-ray diagnostic apparatus according to claim 1, wherein
the monitoring region is specified on the image generated by the processing circuitry such that the monitoring region has a prescribed range corresponding to a point specified on a blood vessel included in the image generated by the processing circuitry.

10. The X-ray diagnostic apparatus according to claim 1, wherein
the monitoring region is specified on the image generated by the processing circuitry such that the monitoring region is on a blood vessel in a prescribed distance from a treatment target portion on the image generated by the processing circuitry.

11. The X-ray diagnostic apparatus according to claim 1, wherein
the processing circuitry sets all the pixels included in the monitoring region as monitoring targets, monitors successive change in signal strength of each of pixels set as the monitoring targets in real time, and determines whether or not the specified condition is satisfied in all pixels set as the monitoring targets.

12. The X-ray diagnostic apparatus according to claim 1, wherein
the processing circuitry sets a plurality of pixels, selected out of pixels included in the monitoring region, as monitoring targets, monitors successive change in signal strength of each of pixels set as the monitoring targets in real time, and determines whether or not the specified condition is satisfied in all pixels set as the monitoring targets.

13. The X-ray diagnostic apparatus according to claim 1, wherein
the processing circuitry determines, based on the feature amount, whether or not the condition is satisfied in all pixels set as monitoring targets.

14. The X-ray diagnostic apparatus according to claim 13, wherein
the feature amount is at least one of: a maximum concentration value at time to peak (TP) when a concentration of the contrast medium is a maximum in a time density curve representative of successive change in the concentration based on the signal strength; and a half-width concentration value that is a half width value of the time density curve, and
the processing circuitry determines that the condition is satisfied when the concentration is lowered by a specified percentage from the maximum concentration value or from the half-width concentration value.

15. The X-ray diagnostic apparatus according to claim 14, wherein
the processing circuitry calculates at least one feature amount out of: the maximum concentration value; the half-width concentration value; mean transit time of the contrast medium, a lower area of the time density curve, a blood flow velocity of the object obtained from the time density curve, a blood flow rate of the object obtained from the time density curve, arrival time of the contrast medium at each of the pixels based on the time density curve, the TP, and a gradient to the maximum concentration value in the time density curve, and the processing circuitry selects any one of the feature amounts, and determines whether or not the specified condition is satisfied based on whether or not a condition for calculating the selected feature amount is satisfied.

16. The X-ray diagnostic apparatus according to claim 15, wherein
the processing circuitry generates, as the parametric image, a color image such that a color corresponding to values of the feature amount are allocated to each pixel of the color image.

17. The X-ray diagnostic apparatus according to claim 2, wherein
the processing circuitry generates the plurality of difference images as a plurality of first difference images, and then sequentially generates a plurality of second difference images based on the X-rays,
determines the monitoring region in the plurality of second difference images based on the plurality of first difference images,
determines whether or not signal strength of each of pixels included in the monitoring region of the plurality of second difference images satisfies the specified condition,
controls the X-ray generator based on a result of the determination so as to reduce a dose of the X-rays for imaging of the plurality of second difference images or to turn off irradiation of the X-rays, and
generates the parametric image based on the feature amount determined by change in signal strength of each of pixels of a part of the plurality of second difference images, the part of the plurality of second difference images being generated before the X-ray generator is controlled based on the result of the determination.

18. The X-ray diagnostic apparatus according to claim 17, wherein
the first difference images are difference images between the mask image generated before the administration of the contrast medium to the object and the contrast images generated after the administration of the contrast medium to the object, the mask image being generated prior to main imaging by X-ray irradiation with a low dose as compared with the main imaging, and
the second difference images are sequentially generated based on the X-rays in the main imaging.

19. The X-ray diagnostic apparatus according to claim 18, wherein
when a plurality of third difference images are further generated in sequence in the main imaging, the processing circuitry monitors successive change in signal strength of each of pixels included in the monitoring region determined based on the first difference images, and
the processing circuitry determines whether or not the signal strength of each of pixels included in the monitoring region in the plurality of third difference images generated in the main imaging satisfies the specified condition, and controls the X-ray generator based on a result of the determination so as to reduce a dose of the X-rays for imaging of the plurality of third difference images or to turn off the X-ray irradiation.

20. An X-ray diagnostic method, comprising:
generating a plurality of contrast images sequentially based on X-rays after administration of a contrast medium to the object, the X-rays being generated by an X-ray generator and irradiating an object;
determining monitoring region in the plurality of contrast images;

monitoring change in signal strength of each of pixels included in the monitoring region of the plurality of contrast images sequentially generated;

determining whether or not the signal strength of each of the pixels included in the monitoring region satisfies a specified condition;

controlling the X-ray generator based on a result of the determination so as to reduce an X-ray dose or to turn off irradiation of the X-rays; and generating a parametric image based on a feature amount determined by change in signal strength of each of pixels of a part of the plurality of contrast images sequentially generated, the part of the plurality of contrast images sequentially generated being generated before the X-ray generator is controlled based on the result of the determination.

* * * * *